United States Patent [19]

Nicholson et al.

[11] Patent Number: 5,641,404
[45] Date of Patent: Jun. 24, 1997

[54] PROCESS FOR THE SEPARATION OF ENANTIOMERS

[75] Inventors: Lawrence W. Nicholson; Christian T. Goralski; Curtis D. Pfeiffer, all of Midland, Mich.

[73] Assignee: The Dow Chemical Company, Midland, Mich.

[21] Appl. No.: 596,338

[22] PCT Filed: Aug. 25, 1994

[86] PCT No.: PCT/US94/09687

§ 371 Date: Feb. 20, 1996

§ 102(e) Date: Feb. 20, 1996

[87] PCT Pub. No.: WO95/05879

PCT Pub. Date: Mar. 2, 1995

Related U.S. Application Data

[63] Continuation-in-part of Ser. No. 112,722, Aug. 27, 1993, abandoned.

[51] Int. Cl.$^6$ .................................................. B01D 15/08
[52] U.S. Cl. .................. 210/635; 210/656; 210/198.2
[58] Field of Search ................................. 210/635, 656, 210/198.2, 502.1

[56] References Cited

U.S. PATENT DOCUMENTS

| | | | |
|---|---|---|---|
| 3,996,246 | 12/1976 | Hoffman | 260/343.6 |
| 4,290,893 | 9/1981 | Hare | 210/656 |
| 4,476,713 | 10/1984 | Alfredson | 210/656 |
| 4,565,877 | 1/1986 | Wada | 210/656 |

FOREIGN PATENT DOCUMENTS

| | | | |
|---|---|---|---|
| 0316270 | 5/1989 | European Pat. Off. | 210/198.2 |

OTHER PUBLICATIONS

Okamoto, Masahiko et al., "Reversal of elution order during direct enantiomeric separation of pyriproxyfen on a cellulose–based chiral stationary phase", *Journal of Chromatography*, 588 (1991) 177–180.

Wainer, Iriving W. et ak,, "Resolution of Enantiomeric Amides on a Cellulose Triben Zoate Chiral Stationary Phase", *Journal of Chromatography*, 388 (1987) 65–74.

Francotte and Wolf, "Benzoyl Cellulose Beads in the Pure Polymeric Form as a NewPowerful Sorbent for the Chromatographic Resolution of Racemates", Chirality, 3(1991) 43–55.

Francotte and Wolf, "Chromatographic resolution on methylbenzoylcelluolose", Journal of Chrom., 595 (1992) 63–75.

Okamoto et al. "Chromatographic Chiral Resolution" Journal of Chromatography, 389 (1987) 95–102.

"Res. of Enantiomers by HPLC on Cellulose Derivatives", 15th Int'l Sym. on Chromatography, Nürnberg (1984 280–284).

Lit. of Daicel Chem. Ind., Ltd. parent co. of Chiral Tech., Inc. labeled "For Superior Chiral Separation, Chiral HPLC Col" pp. 1 and 2 undated.

Synder, Introduction to Modern Liquid Chromatography, John Wiley & Sons, Inc., 1979, New York, pp. 248 and 261–263.

*Primary Examiner*—Ernest G. Therkorn
*Attorney, Agent, or Firm*—Timothy S. Stevens

[57] ABSTRACT

A process for separating enantiomeric mixtures by liquid chromatography using a stationary phase that includes cellulose or amylose derivative and a mobile phase that includes methanol and pentane, the concentration of methanol in the mobile phase being greater than one tenth percent by volume and less than the saturation concentration of methanol in the mobile phase, the concentration of pentane being at least that necessary to resolve the enantiomeric mixture into its enantiomers with a resolution at least one and one half times greater than the pentane of the mobile phase is replaced with hexane.

12 Claims, 1 Drawing Sheet

PROCESS FOR THE SEPARATION OF ENANTIOMERS

This application is a 35 U.S.C. 371 of PCT/UC96/09687, filed Aug. 25, 1994, which, in turn, is a continuation-in-part of U.S. patent application Ser. No. 08/112,722, filed Aug. 27, 1993, now abandoned.

FIELD OF THE INVENTION

The instant invention is in the field of liquid chromatography. In general, liquid chromatography is a method of chemical separation. Most often, liquid chromatographic separations involve components of different molecular formulas. However, in some circumstances, such as the separation of enantiomers, the components to be separated have the same molecular formula.

BACKGROUND

An important goal of chromatography is a complete separation of components in a mixture. Therefore, the field of chromatography is continually striving to increase the efficiency of separating components in order to improve resolution and to permit better isolation of different components.

In particular, there is an increasing demand for the better isolation of enantiomerically pure forms of biologically active chiral compounds in order to investigate relationships between the stereochemistry of these compounds and their biological activity. Therefore, the individual enantiomers should be isolated efficiently, with high optical purity, and in sufficient quantity to perform biological, clinical, or other tests and then, perhaps, to produce commercial amounts of the enantiomer if the test is successful. Chromatography on chiral stationary phases has been recognized as a useful tool in achieving these goals and is now established as an acceptable method for this purpose.

Among the myriad of chiral stationary phases developed and studied since the 1980's, derivatized cellulose-based and amylose-based stationary phases are known to be efficient and versatile chiral sorbents for the chromatographic resolution of enantiomers. Such cellulose-based and amylose-based sorbents show very different selectivities depending on the devitalizing groups on the cellulose and amylose. (Francotte & Wolf, Journal of Chromatography, 595 (1992) 63–75).

The effort to achieve greater separation of enantiomeric mixtures has focused on the stationary phase used, which, as mentioned, is often a cellulose or amylose derivative. However, the mobile phase used for the separation generally is not discussed at length. Typically, the mobile phase used is hexane-isopropanol (9:1). Hexane/ethanol eluents are also known. (Chiral Technologies, Inc.)

With current methods, separation and resolution of enantiomeric mixtures is difficult. Therefore, the art of liquid chromatography would be advanced if greater separation and resolution between enantiomers could be obtained.

SUMMARY OF THE INVENTION

The instant invention is a process for separating enantiomeric mixtures comprising two steps. The first step is to contact a liquid phase with a chiral phase; the liquid phase comprising methanol and pentane such that the concentration of methanol is greater than one tenth percent on a volume basis, and less than or equal to the saturation concentration of methanol in the liquid phase. The second step is to contact an enantiomeric mixture with the chiral phase and with the liquid phase, the concentration of pentane in the liquid phase being at least that necessary to resolve the enantiomeric mixture into its enantiomers with a resolution at least one and one half times greater than when the pentane of the liquid phase is replaced with hexane.

The instant invention is also a process for separating enantiomeric mixtures by column liquid chromatography comprising two steps. The first step is to flow a mobile phase through a column means containing a chiral stationary phase, the mobile phase comprising methanol and pentane such that the concentration of methanol is greater than one tenth percent on a volume basis and less than or equal to the saturation concentration of methanol in the mobile phase. The second step is to introduce an enantiomeric mixture into the column so the enantiomeric mixture flows from the column resolved into its enantiomers, the concentration of pentane in the mobile phase being at least that necessary to resolve the enantiomeric mixture into its enantiomers with a resolution at least one and one half times greater than when the pentane of the mobile phase is replaced with hexane.

DETAILED DESCRIPTION OF THE INVENTION

Figure 1:
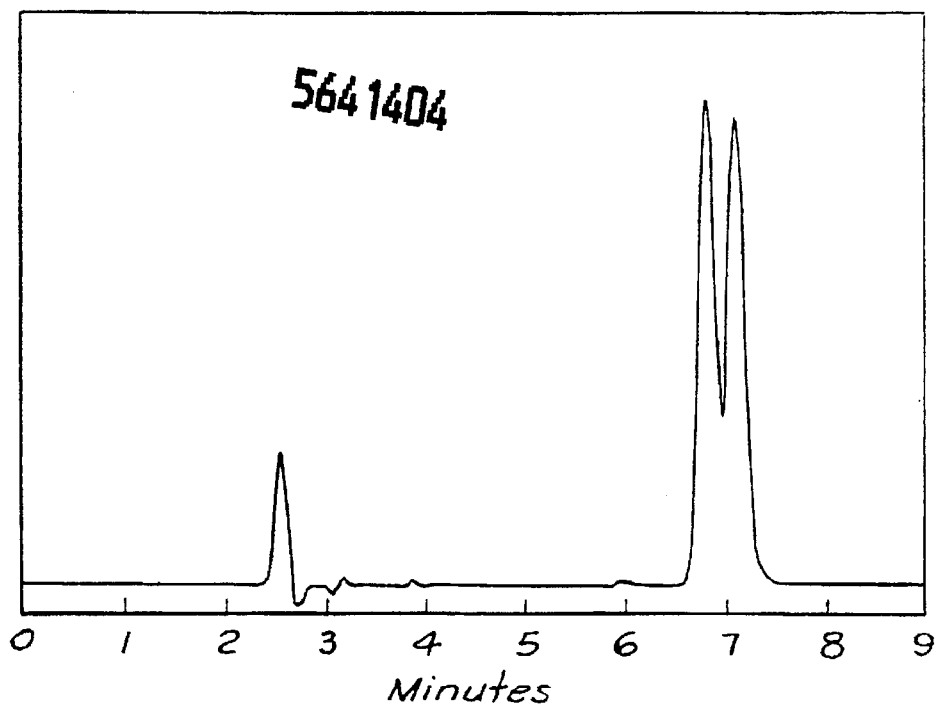
FIG. 1 shows a chromatographic separation of the enantiomers of 2-(naphthyl)-ethanol using a methanol/hexane eluent.

The instant invention is a process for separating enantiomeric mixtures comprising two steps. The first step is to contact a liquid phase with a chiral phase; the liquid phase comprising methanol and pentane such that the concentration of methanol is greater than one tenth percent on a volume basis, and less than or equal to the saturation concentration of methanol in the liquid phase. The second step is to contact an enantiomeric mixture with the chiral phase and with the liquid phase, the concentration of pentane in the liquid phase being at least that necessary to resolve the enantiomeric mixture into its enantiomers with a resolution at least one and one half times greater than when the pentane of the liquid phase is replaced with hexane.

For purposes of the instant invention, a perfect or one hundred percent separation or resolution of the enantiomers is not required, a separation in part, such as a fifty percent separation or even a ten percent separation is sufficient. However, the resolution of the enantiomers must be at least one and one half times greater than when the pentane of the liquid phase is replaced with hexane.

The term "resolution" is well understood in the art of liquid chromatography and is equal to the difference between the chromatographic elution times (or elution volumes or their equivalent) of the enantiomers times two, divided by the sum of the triangulated chromatographic peak widths (or their equivalents) of the enantiomers at the baseline of the chromatogram (or its equivalent). By way of explanation, if the resolution of two enantiomers is two when the pentane of the instant invention is replaced with hexane, then the resolution of the enantiomers must be three or more when pentane is used. Preferably, the resolution of the enantiomers is at least two times better than when the pentane of the liquid phase is replaced with hexane. More preferably, the resolution of the enantiomers is at least two and one half times better than when the pentane of the liquid phase is replaced with hexane.

The term "liquid phase" refers to a liquid comprising methanol and pentane such that the concentration of methanol is greater than one tenth percent on a volume basis, and less than or equal to the saturation concentration of methanol in the liquid phase. Preferably, the concentration of methanol in the liquid phase is greater than two percent by volume. In addition, preferably the concentration of pentane in the liquid phase is at least ten percent by volume and more preferably the concentration of pentane in the liquid phase is at least twenty five or fifty percent. In many applications the liquid phase should consist essentially of methanol and pentane.

The term "saturation concentration" means the maximum equilibrium quantity of methanol in the liquid phase at a given temperature such that a homogeneous mixture is maintained. When phase separation begins, the "saturation concentration" has been reached. More specifically, beyond the "saturation concentration" the performance of the system for separation of enantiomers decreases substantially. This decreased performance may be due to a coating of one of the solvents of the liquid phase covering the chiral phase such that the chiral phase is less able to efficiently adsorb or absorb components of interest from the sample.

The term "chiral phase" refers to a phase which selectively adsorbs or absorbs components of interest from an enantiomeric mixture in a liquid phase, comprising methanol and pentane, such that the enantiomers are separated at least in part. Preferably, the chiral phase comprises a polysaccharide derivative. The term "polysaccharide" means a combination of two or more monosaccharides bonded together. More preferably, the polysaccharide is made up of a combination of five or more monosaccharides bonded together. A "derivative" is a chemical substance related structurally to another substance and theoretically derivable from it. Preferably, the "polysaccharide derivative" used as a chiral phase is selected from the group consisting of cellulose and amylose derivatives. Most preferably, the polysaccharide derivative is selected from the group consisting of a cellulose ester derivative with $CO(C_6H_4)CH_3$, $COC_6H_5$, $COCH_3$, or $COCHCH(C_6H_5)$ groups; a cellulose carbamate derivative with $CONH(C_6H_3)$ $(CH_3)_2$, $CONH(C_6H_5)$, $CONH(C_6H_4)CH_3$, or $CONH(C_6H_4)Cl$ groups; and an amylose derivative with $CONHCH(CH_3)$ $(C_6H_5)$ or $CONH(C_6H_3)(CH_3)_2$ groups. Such stationary phases can be purchased commercially from Chiral Technologies, Inc., 730 Springdale Drive, Drawer I, Exton, Pa. 19341. The chiral phase may also comprise a cyclodextrin derivative.

The instant invention is also a process for separating enantiomeric mixtures by column liquid chromatography comprising two steps. The first step is to flow a mobile phase through a column means containing a chiral stationary phase; the mobile phase comprising methanol and pentane such that the concentration of methanol is greater than one tenth percent on a volume basis and less than or equal to the saturation concentration of methanol in the mobile phase. The second step is to introduce an enantiomeric mixture into the column so the enantiomeric mixture flows from the column separated into its enantiomers, the concentration of pentane in the mobile phase being at least that necessary to resolve the enantiomeric mixture into its enantiomers with a resolution at least one and one half times greater than when the pentane of the liquid phase is replaced with hexane. Preferably the resolution is at least two times greater than when the pentane of the liquid phase is replaced with hexane. Most preferably the resolution is at least two and one half times greater than when the pentane of the liquid phase is replaced with hexane.

The term "mobile phase" refers to an eluent chosen to work with a column means as described below such that the combination is capable of separating enantiomers, at least partially. As described, the mobile phase of the instant invention comprises methanol and pentane such that the concentration of methanol is greater than one tenth percent on a volume basis, and less than or equal to the saturation concentration, as defined above, of methanol in the mobile phase. Preferably, the concentration of methanol in the mobile phase is greater than two percent by volume. In addition, preferably the concentration of pentane In the mobile phase is at least ten percent by volume and more preferably the concentration of pentane in the mobile phase is at least twenty five or fifty percent. In many applications the mobile phase should consist essentially of methanol and pentane.

The term "column means" refers to a packed column or any standard stationary phase container or support which may be used in column liquid chromatography for chiral separations. For purposes of defining an appropriate column for a given application, the teachings of literature of Daicet Chemical Industries, Ltd., the parent company of Chiral Technologies, Inc. labeled, "For Superior Chiral Separation, Chiral HPLC Column", are incorporated by reference.

Similar to the term "chiral phase" described above, the term "chiral stationary phase" refers to a stationary phase which selectively adsorbs or absorbs components of interest from an enantiomeric mixture in a mobile phase comprising an alcohol and a solvent such that the enantiomers are separated at least in part. A theory used to describe such separation by contacting a mobile phase with a stationary phase involves the repeated adsorption or absorption and deadsorption or deabsorption of the components of a mixture by the stationary phase. Under this theory, the components of the mixture traveling in the mobile phase come into contact with and are adsorbed or absorbed by the stationary phase, and, subsequently, are deadsorbed or deabsorbed from the stationary phase to travel once again in the mobile phase until they contact another part, or a successive stage, of the stationary phase. Different components are adsorbed or absorbed and deadsorbed or deabsorbed at different rates which results in at least a partial separation of the components.

Preferably, the chiral stationary phase comprises a polysaccharide derivative. More preferably, this "polysaccharide derivative" is selected from the group consisting of cellulose and amylose derivatives. Most preferably, the polysaccharide derivative is selected from the group consisting of a cellulose ester derivative with $CO(C_6H_4)CH_3$, $COC_6H_3$, $COCH_3$, or $COCHCH(C_6H_5)$ groups; a cellulose carbamate derivative with $CON H(C_6H_3)(CH_3)_2$, $CONH (C_6H_5)$, $CONH(C_6H_4)CH_3$, or $CONH(C_6H_4)Cl$ groups; and an amylose derivative with $CONHCH(CH_3)(C_6H_5)$ or $CONH(C_6H_3)(CH_3)_2$ groups. Such stationary phases can be purchased commercially from Chiral Technologies, Inc., 730 Springdale Drive, Drawer 1, Exton, Pa. 19341. The stationary phase may also comprise a cyclodextrin derivative.

For purposes of describing polysaccharide derivatives used as chiral stationary phases and cellulose-based stationary phases, the teachings of the following are incorporated by reference: Francotte and Wolf, "Benzoyl Cellulose Beads in the Pure Polymeric Form as a New Powerful Sorbent for the Chromatographic Resolution of Racemates", Chirality, 3 (1991) 43–55; Francotte and Wolf, "Chromatographic resolution on methylbenzoylcellulose beads", Journal of Chromatography, 595 (1992) 63–75; Okamoto, Aburatani and Hataria, "Chromatographic Chiral Resolution", Journal of Chromatography, 389 (1987) 95–102; Ichida et al., "Resolution of Enantiomers by HPLC on Cellulose Derivatives", Presented at the 15th International Symposium on Chromatography, Nürnberg (1984) 280–284.

It should be understood that not all enantiomers are better separated by the instant invention than when the hexane of a liquid or mobile phase is replaced by pentane. No theory has been formulated to confidently predict which enantiomers are better separated by the instant invention. However, in many applications the improvement in the resolution of enantiomers is substantial.

EXAMPLE 1

A five volume percent methanol/ninety-five volume percent n-pentane eluent, i.e., mobile phase, is prepared. This eluent is pumped through the following elements at a flow rate of one milliliter per minute using a liquid chromatography pump: (1) a sample injection valve having a twenty microliter injection volume; (2) a twenty-five centimeter long, 4.6 millimeter internal diameter Chiralpak® AD brand column from Chiral Technologies, Inc., which contains an amylose derivative adsorbent ($CONH(C_6H_3)(CH_3)_2$ groups); and (3) an ultraviolet liquid chromatography detector set to detect at 210 nanometers and having a sensitivity of 1 absorbance unit per volt. The detector is connected to a Nelson Analytical chromatographic computer having a printer for printing data and for producing chromatograms.

Figure 2:
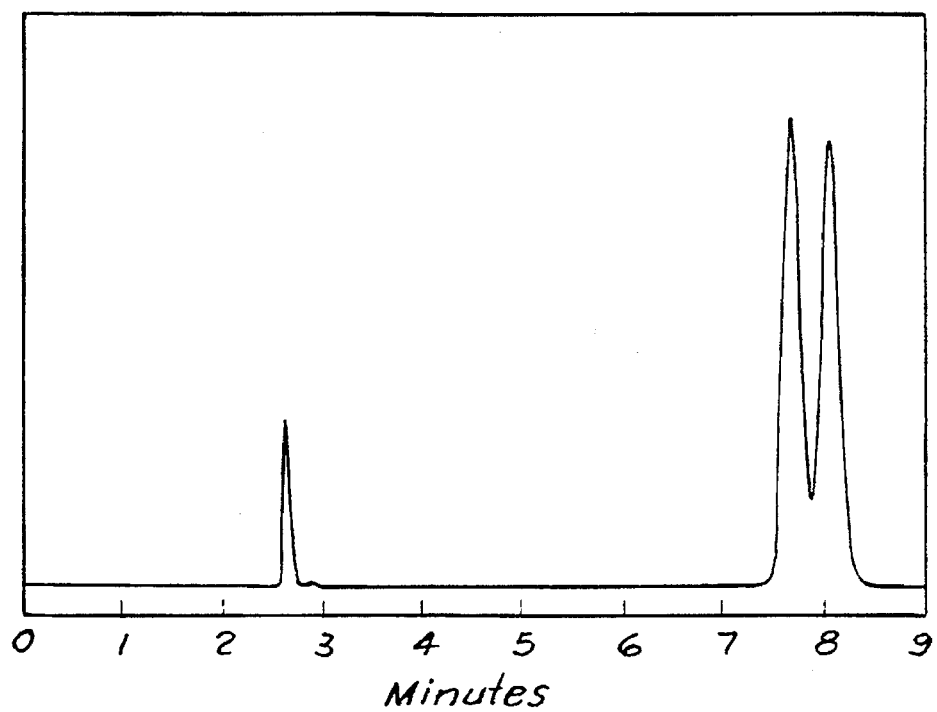
FIG. 2 shows the chromatographic separation of the enantiomers of 2-(naphthyl)-ethanol using a methanol/pentane eluent.

An 18 part per million by weight solution of the enantiomers of 2-(naphthyl)-ethanol is prepared in this eluent. Twenty microliters (about three hundred and sixty nanograms) of the enantiomers are injected. A chromatogram is produced and it is reproduced in FIG. 2. The resolution of the enantiomers in FIG. 2 is determined to be 0.99.

The pentane of the eluent is replaced with hexane. The above mixture of enantiomers is injected again. A chromatogram is produced and it is reproduced in FIG. 1. The resolution of the enantiomers in FIG. 1 is determined to be 0.56. The improvement in the resolution of the enantiomers when pentane is used in the eluent instead of hexane is thus 0.99 divided by 0.56 or 1.77.

EXAMPLE 2

The apparatus of Example 1 is used with an eluent of five volume percent methanol/ninety-five volume percent n-pentane at a flow rate of two milliliters per minute. A seven hundred and ninety part per million by weight solution of the enantiomers of 5-methyl-5-phenylhydantoin is prepared in this eluent. Twenty microliters (about sixteen micrograms) of the enantiomers are injected. A chromatogram is produced and the resolution of the enantiomers is determined to be 14.73.

The pentane of the eluent is replaced with hexane. The above mixture of enantiomers is injected again. A chromatogram is produced and the resolution of the enantiomers is determined to be 7.92. The improvement in the resolution of the enantiomers when pentane is used instead of hexane is thus 14.73 divided by 7.92 or 1.86.

What is claimed is:

1. A process for separating enantiomeric mixtures, comprising the steps of:
   (a) contacting a liquid phase with a chiral phase, the liquid phase comprising methanol and pentane, the concentration of methanol being greater than one tenth percent on a volume basis and less than or equal to the saturation concentration of methanol in the liquid phase; and
   (b) contacting an enantiomeric mixture with the chiral phase and with the liquid phase, the concentration of pentane in the liquid phase being at least that necessary to resolve the enantiomeric mixture into its enantiomers with a resolution at least one and one half times greater than when the pentane of the liquid phase is replaced with hexane.

2. The process of claim 1, wherein the chiral phase comprises a polysaccharide derivative.

3. The process of claim 2, wherein the polysaccharide derivative is selected from the group consisting of cellulose and amylose derivatives.

4. The process of claim 3, wherein the polysaccharide derivative is selected from the group consisting of a cellulose ester derivative with $CO(C_6H_4)CH_3$, $COC_6H_5$, $COCH_3$, or $COCHCH(C_6H_5)$ groups; a cellulose carbamate derivative with $CONH(C_6H_3)(CH_3)_2$, $CONH(C_6H_5)$, $CONH(C_6H_4)CH_3$, or $CONH(C_6H_4)Cl$ groups; and an amylose derivative with $CONHCH(CH_3)(C_6H_5)$ or $CONH(C_6H_3)(CH_3)_2$ groups.

5. The process of claim 3, wherein the concentration of methanol in the liquid phase is greater than two percent by volume and the liquid phase consists essentially of methanol and pentane.

6. The process of claim 1, wherein the concentration of methanol in the liquid phase is greater than two percent by volume and the liquid phase consists essentially of methanol and pentane.

7. A process for separating enantiomeric mixtures by column liquid chromatography, comprising the steps of:
   (a) flowing a mobile phase through a column means containing a chiral stationary phase, the mobile phase comprising methanol and pentane, the concentration of methanol being greater than one tenth percent on a volume basis and less than or equal to the saturation concentration of methanol in the mobile phase; and
   (b) introducing an enantiomeric mixture into said column means so the enantiomeric mixture flows from the column means resolved into its enantiomers, the concentration of pentane in the mobile phase being at least that necessary to resolve the enantiomeric mixture into its enantiomers with a resolution at least one and one half times greater than when the pentane of the mobile phase is replaced with hexane.

8. The process of claim 7, wherein the chiral stationary phase comprises a polysaccharide derivative.

9. The process of claim 8, wherein the polysaccharide derivative is selected from the group consisting of cellulose and amylose derivatives.

10. The process of claim 9, wherein the polysaccharide derivative is selected from the group consisting of a cellulose ester derivative with $CO(C_6H_4)CH_3$, $COC_6H_5$, $COCH_3$, or $COCHCH(C_6H_5)$ groups; a cellulose carbamate derivative with $CONH(C_6H_3)(CH_3)_2$, $CONH(C_6H_5)$, $CONH(C_6H_4)CH_3$, or $CONH(C_6H_4)Cl$ groups; and an amylose derivative with $CONHCH(CH_3)(C_6H_5)$ or $CONH(C_6H_3)(CH_3)_2$ groups.

11. The process of claim 9, wherein the concentration of methanol is greater than two percent by volume and the liquid phase consists essentially of methanol and pentane.

12. The process of claim 7, wherein the concentration of methanol is greater than two percent by volume and the liquid phase consists essentially of methanol and pentane.

* * * * *